United States Patent [19] [11] Patent Number: 4,640,919
Mochida et al. [45] Date of Patent: Feb. 3, 1987

[54] 3-SUBSTITUTED CARBACEPEM COMPOUNDS HAVING ANTIBACTERIAL EFFECT

[75] Inventors: Kenichi Mochida, Hiratsuka; Takehiro Ogasa; Junichi Shimada, both of Machida; Tadashi Hirata, Yokohama; Kiyoshi Sato, Mishima; Ryo Okachi, Shizuoka, all of Japan

[73] Assignee: Kyowa Hakko Kogyo Co., Ltd., Tokyo, Japan

[21] Appl. No.: 702,623

[22] Filed: Feb. 19, 1985

[30] Foreign Application Priority Data

Feb. 21, 1984 [JP] Japan ............................... 59-30988

[51] Int. Cl.$^4$ .................. A61K 31/53; C07D 251/00; C07D 253/00
[52] U.S. Cl. .................................. 514/241; 514/256; 514/269; 514/299; 544/180; 544/216; 544/242; 544/298; 544/319; 546/183
[58] Field of Search ............... 546/183; 514/299, 241, 514/256, 269; 544/180, 216, 242, 298, 319

[56] References Cited

U.S. PATENT DOCUMENTS 4,123,528 10/1978 Cama et al. .................... 546/183
4,226,866 10/1980 Christensen et al. ............ 546/183
4,278,793 7/1981 Dürchheimer et al. .......... 546/183
4,291,164 9/1981 Hirata et al. ................... 546/183

FOREIGN PATENT DOCUMENTS 0014476 8/1980 European Pat. Off. .
0138396 10/1980 Japan .
0016491 2/1981 Japan .

OTHER PUBLICATIONS

Meiji Seika Kaisha Ltd., Chem. Abst., 100-22506e.
Kyowa Hakko Kogyo Co. Ltd., Chem. Abst., 101-230239t.
Kyowa Hakko Kogyo Co. Ltd., Chem. Abst., 102-60-56u.
Hirata et al., Chem. Abst., 94-121355u, ref. EP 14476.
Uyeo et al, Chem. Abst., 94-65399x.
Kyowa Hakko Kogyo Co. Ltd., Chem. Abst., 97-72181k.
Hirata, Chem. Abst., 100-22505d.
Christensen et al, Chem. Abst., 81-37560f.
Hirata et al, Chem. Abst., 93-239247t, ref. GB 2041923.
Uyeo et al, Chem. Abst., 93-26243b.
Hirata, Chem. Abst., 94-101305z.
Helvetica Chimica Acta, vol. 58, Fasc. 8 (1975), No. 262-263, pp. 2437-2451.
Helvetica Chemica Acta, 57, 1919 (1974).
J. Amer. Chem. Soc., 96, 4986.
Chem. Parm. Bull., 28 (5), 1563-1577.

*Primary Examiner*—Donald G. Daus
*Assistant Examiner*—Cecilia Shen
*Attorney, Agent, or Firm*—Fitzpatrick, Cella, Harper & Scinto

[57] ABSTRACT

Carbacephem compounds represented by the formula:

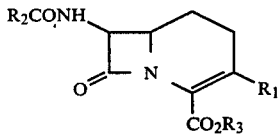

[wherein $R_1$ is a lower alkylsulfonyloxy, unsubstituted or substituted arylsulfonyloxy, azido, cyano, carbamoyloxy, unsubstituted or substituted heterocyclic thio ("heterocyclic" means a 5- or 6-membered heterocyclic group having 1 to 4 O, S or N atoms), unsubstituted or substituted lower alkylthio, or unsubstituted or substituted arylthio group; $R_2$ and $R_3$ are groups frequently used in the cephalosporin chemistry] have strong antibacterial activity against Gram-positive and Gram-negative bacteria, and are useful for curing various infections.

3 Claims, No Drawings

3-SUBSTITUTED CARBACEPEM COMPOUNDS HAVING ANTIBACTERIAL EFFECT

BACKGROUND OF THE INVENTION

The present invention relates to a carbacephem compound having a characteristic electronegative group at the 3-position and a pharmaceutical composition containing the compound.

Heretofore, many patent applications have been filed for the carbacephem compounds, among which those concerning compounds having a 3-positioned substituent include GB No. 2041923A for a compound represented by the formula:

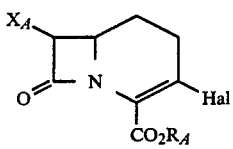

(wherein $X_a$ is an amino, azido, or protected amino group; Hal is halogen; $R_A$ is hydrogen or a carboxyl-protective group); EP No. 0014475A1 for an optically active isomer of compound represented by the formula:

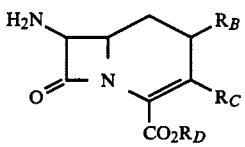

(wherein $R_B$ is hydrogen or an alkyl group; $R_C$ is hydrogen or halogen; $R_D$ is hydrogen or a carboxyl-protective group); EP No. 0014476A1 for an optical active isomer of compound represented by the formula:

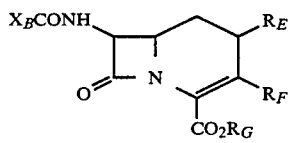

(wherein $X_B$ is a group of

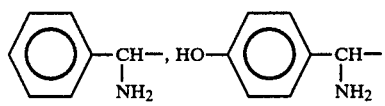

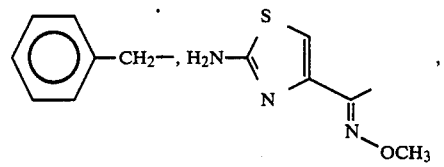

or the like; $R_E$ is hydrogen or an alkyl group; $R_F$ is hydrogen or halogen; $R_G$ is hydrogen or a carboxyl-protective group), etc. In addition, a compound represented by the formula:

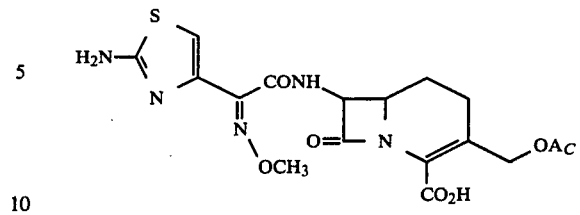

is nominally disclosed in U.S. Pat. No. 4,278,793, column 153.

Compounds of the present invention have a strong antibacterial effect on Gram-negative bacteria and also on Gram-positive bacteria.

DETAILED DESCRIPTION OF THE INVENTION

The present invention relates to a carbacephem compound represented by the formula (I):

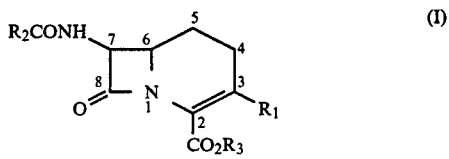

(I)

[wherein $R_1$ is a lower alkylsulfonyloxy, unsubstituted or substituted arylsulfonyloxy, azido, cyano, carbamoyloxy, unsubstituted or substituted heterocyclic thio ("heterocyclic" is a 5- or 6-membered heterocyclic group containing 1 to 4 O, S or N atoms), unsubstituted or substituted lower alkylthio, or unsubstituted or substituted arylthio group; $R_2$ is a group represented by the formula:

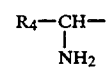

(wherein $R_4$ is an unsubstituted or substituted phenyl, or 2-aminothiazolyl group), or a group represented by the formula:

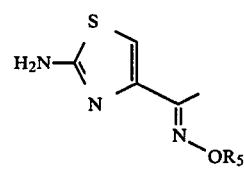

(wherein $R_5$ is an unsubstituted or substituted lower alkyl group); $R_3$ is hydrogen, an alkali metal, an alkaline earth metal, an organic ammonium group, or an ester residue][ the compound will be hereinafter referred to as Compound (I) and other compounds with formula numbers will be hereinafter likewise identified], also to a carbacephem compound represented by the formula (II):

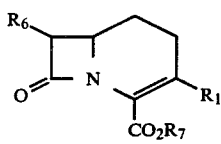

(II)

(wherein $R_1$ has the same meaning as defined above; $R_6$ is a phthalimido, azido or amino group; $R_7$ is hydrogen, an unsubstituted or substituted benzyl, benzhydryl, or lower alkyl group), and further to a pharmaceutical composition containing a Compound (I) as an active ingredient.

In the definition of $R_1$ in the general formula (I), the lower alkylsulfonyloxy includes a straight or branched lower alkylsulfonyloxy group having 1 to 6 carbon atoms, for example, methanesulfonyloxy, ethanesulfonyloxy, propanesulfonyloxy, etc.

In the definition of $R_1$, the arylsulfonyloxy includes benzenesulfonyloxy, α- or β-naphthalenesulfonyloxy, etc., and the substituent means those on the aryl part and includes straight or branched lower alkyl group having 1 to 6 carbon atoms (methyl, ethyl, etc.), hydroxyl, amino, nitro, carboxyl, etc.

In the definition of $R_1$, the heterocyclic group of heterocyclic thio is any of 5- or 6-membered heterocyclic groups having 1 to 4 O, S, or N atoms as defined above, and can desirably be exemplified by pyridyl, tetrazolyl, thiazolyl, thiadiazolyl, oxazolyl, triazolyl, pyrimidyl, imidazolyl, triazinyl, etc. N in these heterocycles is in the form of quaternary ammonium salt, and the counterion is exemplified by —$CO_2$— as the ionized —$CO_2R_3$ at position 2, etc. The substituent on these heterocycles includes a straight or branched lower alkyl group having 1 to 6 carbon atoms (methyl, ethyl, etc.), hydroxyl, amino, nitro, —$(CH_2)_nY$ (wherein Y is a hydroxyl, carboxyl or sulfo group; n is an integer of 1 to 4), etc.

In the definition of $R_1$, the lower alkylthio includes a lower alkylthio group having 1 to 7 carbon atoms (methylthio, ethylthio, etc.), and the substituent means those on the lower alkyl part and includes hydroxyl, carboxyl, sulfo, amino, etc.

In the definition of $R_1$, the arylthio includes phenylthio, α- or β-naphthylthio, etc., and the substituent means those on the aryl part and includes a straight or branched lower alkyl group having 1 to 6 carbon atoms (methyl, ethyl, etc.), hydroxyl, amino, nitro, carboxyl, etc.

In the definition of $R_4$ as regards the definition of $R_2$, the substituent on the phenyl includes the same groups as the substituents on the aryl part of said arylthio group. In the definition of $R_5$ as regards the definition of $R_2$, the lower alkyl includes a straight or branched lower alkyl group having 1 to 7 carbon atoms (methyl, ethyl, etc.), and the substituent includes hydroxyl, carboxyl, sulfo, etc.

In the definition of $R_3$, the alkali metal includes sodium, potassium, etc., the alkaline earth metal includes calcium, magnesium, etc., and the organic ammonium group includes ammonium groups of organic amines such as basic amino acids.

In the definition of $R_3$, the ester residue includes groups relatively readily releasable in vivo, represented by the formula:

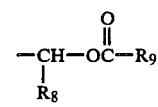

(wherein $R_8$ is hydrogen or a lower alkyl group having 1 to 6 carbon atoms; $R_9$ is a lower alkyl group having 1 to 6 carbon atoms, or phenyl), or by the formula:

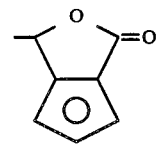

In the definition of $R_7$ in the general formula (II), the substituent on the benzylphenyl includes a straight or branched lower alkyl group having 1 to 6 carbon atoms (methyl, ethyl, etc.), hydroxyl, amino, nitro, carboxyl, etc. In the definition of $R_7$, the lower alkyl includes a straight or branched lower alkyl group having 1 to 8 carbon atoms, for example, methyl, ethyl, t-butyl, etc.

Processes for preparing compounds (I) and (II) is described below:

Compounds (I), and (II) can be synthesized according to the following step formulae:

Step formula 1

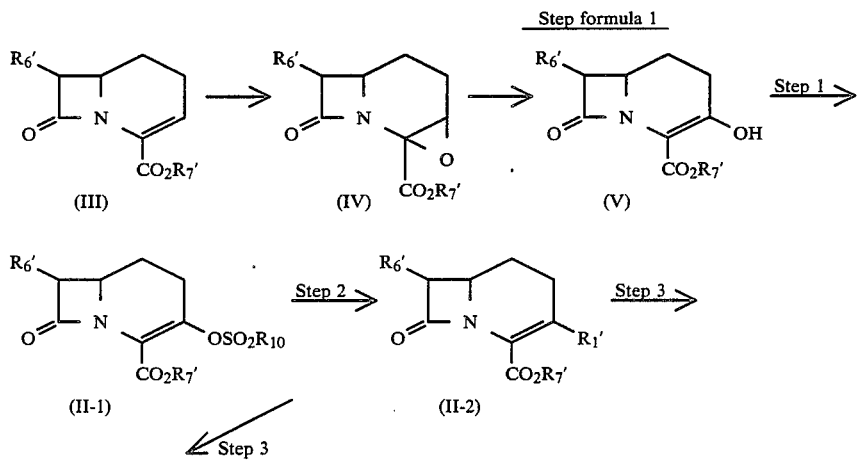

-continued
Step formula 1

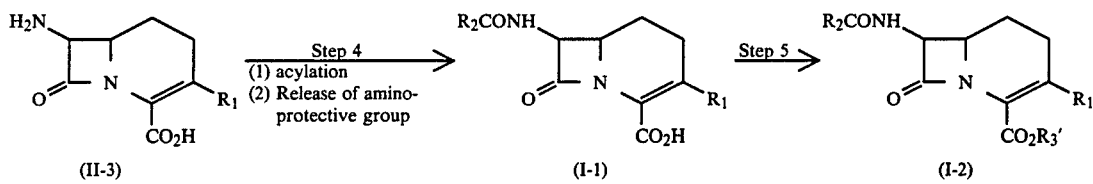

Step formula 2

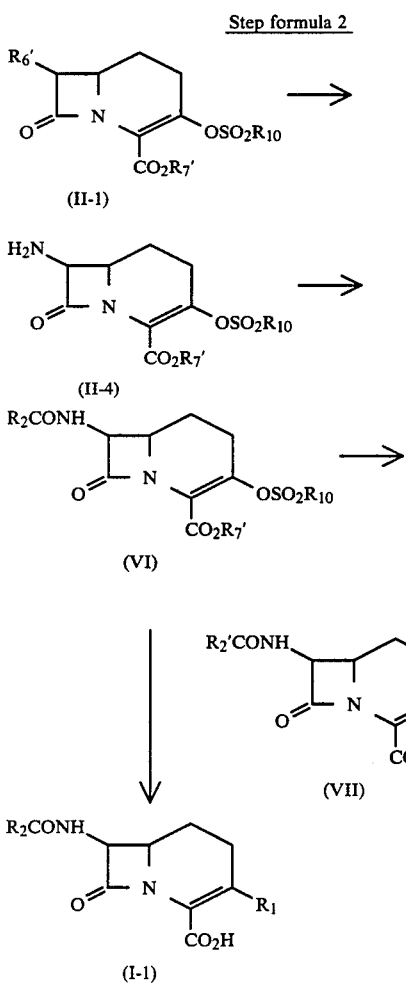

[wherein $R_6'$ is $R_6$ excluding amino, that is, phthalimido, or amido; $R_7'$ excluding hydrogen; $R_{10}$ is a lower alkyl group or an unsubstituted or substituted aryl group; $R_1'$ is $R_1$ excluding $-OSO_2R_{10}$; $R_3'$ is $R_3$ excluding hydrogen; $R_2'$ is an amino-protected $R_2$; formulae (II-1) to (II-4) are covered by formula (II); formulae (I-1) and (I-2) are covered by formula (I)].

In the preparation of Compounds (I) and (II), Compound (V) as a 3-hydroxycarbacemphem compound can be used as a starting compound. Route from Compound (III) (which and whose process are described in GB No. 2017102A) to Compound (V) through Compound (IV) as an epoxy compound is described in detail in Japanese Patent Application No. 200034/82. Another process for synthesizing 3-hydroxycarbacephems such as Compound (V) is described in Chem. Pharm. Bull., 28 (5), 1563 (1980).

Step 1

Compound (V) is allowed to react with an active derivative of sulfonic acid represented by the formula $R_{10}SO_3H$ (wherein $R_{10}SO_2$—O— has the same meaning as the lower alkylsulfonyloxy or unsubstituted or substituted arylsulfonyloxy in the definition of $R_1$), for example, an acid chloride or acid anhydride, in an inert solvent in the presence of a base, whereby Compound (II-1) is obtained. As the inert solvent, methylene chloride, chloroform, ether, tetrahydrofuran, ethyl acetate, benzene, toluene, dimethylformamide, etc. can be used. As the base, tertiary amines such as triethylamine, N-methylmorpholine, pyridine, dimethylaminopyridine, etc. can be used. An appropriate amount of the base is approximately an equivalent amount to the active derivative. An appropriate reaction temperature is from $-78°$ C. to room temperature.

After the end of reaction, Compound (II-1) is isolated and purified by crystallization, column chromatography such as silica gel column chromatography, etc. The reaction mixture can be used as such in the successive step.

Step 2

Compound (II-1) is allowed to react with a compound of formula $R_1'H$ or $R_1'X$ (wherein $R_1'$ has the same meaning as defined above; X is an alkali metal such as sodium, potassium, etc., or an organic ammonium such as triethylammonium, ammonium of diazabicycloundecene, etc.) in an inert solvent, whereby Compound (II-2) can be obtained. As the inert solvent, methylene chloride, chloroform, tetrahydrofuran, dimethylformamide, dimethylsulfoxide, etc. can be used.

An appropriate amount of $R_1'H$ or $R_1'X$ compound is at least an equivalent amount, particularly 1 to 4 equivalent amounts to Compound (II-1). An appropriate reaction temperature is 0° to 100° C.

$R_1'X$ can be prepared by bringing $R_1'H$ into contact with a metal hydride such as sodium hydride, potassium hydride, etc. or with an organic amine in said inert solvent.

Step 3

This step is a step of removing the protective group from Compound (II-2) or (II-1) to obtain Compound (II-3). The deprotection can be carried, out without impairing the functional group in Compounds (II-2) and (II-1) according to the procedure frequently used in the cephalosporin chemistry. When $R_7'$ is, for example, t-butyl or benzhydryl as an ester residue, carboxyl can be formed by using trifluoroacetic acid, formic acid, etc., and when $R_7'$ is paranitrobenzyl or benzhydryl, carboxyl can be formed by catalytic reduction. When the substituent represented by $R_6'$ is azido, it can be converted to amino by catalytic reduction or by action of hydrogen sulfide in the presence of a base such as triethylamine, etc. When the substituent represented by $R_6'$ is phthalido, it can be converted to amino according to the procedure using a hydrazine compound disclosed in Japanese Published Unexamined Patent Application No. 91991/1982. Deprotection of $R_6'$ and $R_7'$ can be carried out without any preference thereto, but it is preferable to make conversion to carboxyl at first, and then to amino.

Step 4

This step is a step of acylating Compound (II-3) with a carboxylic acid represented by $R_2'$ $CO_2H$ (wherein $R_2'$ has the same meaning as defined above) or its reactive derivative and then removing the acyl-protective group from $R_2'$ to obtain Compound (I-1). As the aminoprotective group in $R_2'$, any of the protective groups usually used in the cephalosporin chemistry can be used, and trityl, t-butoxycarbonyl, etc. are preferable. As the reactive derivative, acid chlorides, mixed acid anhydrides, various active esters, etc. can be mentioned. As the reaction procedures for both acylation and deprotection, those frequently used in the synthesis of cephalosporins are used. When the carboxylic acid represented by $R_2CO_2H$ is a carboxylic acid such as phenylgrycine or parahydroxyglycine, acylation can also be carried out according to a procedure using an enzyme disclosed in Japanese Published Unexamined Patent Application No. 138396/1980(equate EP No. 14476) and EP No. 0014476A1.

Step 5

Compound (II-2) can be derived from Compound (I-1), if necessary, according to the conventional procedure through reaction with various inorganic and organic bases, or through esterification.

Another procedure:

It is preferable to synthesize Compound (I) according to the foregoing procedures, but it can also be synthesized according to Step formula 2. That is, Compound (II-1) is converted to Compound (II-4) according to the procedure mentioned in Step 3, then to Compound (VI) by acylation according to the procedure mentioned in Step 4, and to Compound (VII) according to the procedure mentioned in Step 2. Then, Compound (VI) or (VII) is converted to Compound (I-1) according to the procedure mentioned in Step 3. In that case, removal of the amino protective group from $R_2'$ can be carried out in another manner, but when the amino-protective groups are trityl, t-butoxycarbonyl, etc., they can be removed at the same time under the conditions of Step 3.

The compounds of the present invention have a strong antibacterial activity against Gram-positive and Gram-negative bacteria, and are useful for curing various infections, as a sterilizer and as an antiseptic component.

Thus, the invention includes within its scope pharmaceutical compositions comprising, as an active ingredient, a Compound (I) in association with a pharmaceutical carrier or diluent. The compounds of this invention are administered by parenteral (intramuscular, intraperitoneal, intravenous or subcutaneous injection routes), oral or rectal route of administration and can be formulated in dosage forms appropriate for each route of administration.

Preparations according to this invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions or by heating the compositions. They can also be manufactured in the form of sterile solid compositions which can be dissolved in sterile water or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth or polyvinyl-pyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agent such as sodium lauryl sulfate. The tablets may be coated according to methods well known in the art. Oral liquid preparations may be in the form of aqueous or oily suspension, solution, emulsions, syrups, etc., or may be presented as a dry product, for reconstitution with water or other suitable vehicle before use. Such liquid preparations may contain conventional additive such as suspending agents, for example, sorbitol syrup, methyl cellulose, glucose sugar syrup, gelatin, hydroxyethylcellulose, carboxymethylcellulose, aluminum stearate gel, emulsifying agents, for example, lecithin or sorbitan monooleate; non-aqueous vehicles, which may include edible oils, for example, almond oil, coconut oil, propylene glycol or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 and 350 mg/kg of body weight daily are administered to mammalian patients to achieve an antibiotic effect.

The present invention is further described below, referring to Examples and Reference Examples.

EXAMPLE 1

Preparation of tertiary butyl ester of (±)-cis-7-phthalimido-3-methanesulfonyloxy-1-azabicyclo [4.2.0]oct-2-en-8-oxo-2-carboxylic acid At first, 12.2 g of tertiary butyl ester of (±)-cis-7-phthalimido-1-azabicyclo [4.2.0]oct-2,3-epoxy-8-oxo-2-carboxylic acid obtained in Reference Example 1 is suspended in 245 ml of toluene, and a catalytic amount of p-toluenesulfonic acid is added thereto. The suspension is heated at 110° C. A uniform solution is obtained after 20 minutes, and then the solution is immediately cooled. Then, 200 ml of ethyl acetate is added thereto at room temperature, and the mixture is washed with water, an aqueous saturated sodium bicarbonate solution and an aqueous saturated sodium chloride solution. The organic layer is dried over anhydrous sodium sulfate and the solvent is removed therefrom by distillation under reduced pressure. The thus obtained light yellow solid is dissolved in 230 ml of anhydrous methylene chloride, and the solution is cooled to −50° to −40° C. Then, 2.8 ml of methanesulfonyl chloride and 5.0 ml of triethylamine are added thereto, and the mixture is subjected to reaction at the same temperature for one hour. The reaction solution is diluted with chloroform, and washed successively with water, an aqueous 10% citric acid solution, water, an aqueous saturated sodium bicarbonate solution, and the organic layer is dried over anhydrous sodium sulfate. The solvent is removed therefrom by distillation under reduced pressure, whereby light yellow crystals are obtained. The crystals are thoroughly washed with a solvent mixture of hexane:ethyl acetate=1:1, whereby 9.2 g of white needle-like crystals are obtained. The crystals have the following physical properties and are identified to be the captioned compound (yield: 62.7%).

NMR (CDCl$_3$) δ (ppm): 6.8 (4H, m), 5.60 (1H, d, J=5.2 Hz), 4.0 (1H, m), 3.27 (3H, s), 2.8–1.8 (4H, m), 1.57 (9H, s).

IR ν max (KBr) (cm$^{-1}$): 1800, 1790, 1775, 1725, 1395.

EXAMPLE 2

Preparation of tertiary butyl ester of (±)-cis-7-phthalimido-3-(1-methyl-1,2,3,4-tetrazol-5-yl)-thio-1-azabicyclo [4.2.0] oct-2-en-8-oxo-2-carboxylic acid At first, 360 mg of sodium hydride (50%) is suspended in 10 ml of dried dimethylformamide, and 1.2 g of 1-methyl-5-mercapto-1,2,3,4-tetrazole is added thereto to make a solution. Then, 1.2 g of tertiary butyl ester of (±)-cis-7-phthalimido-3-methanesulfonyloxy-1-azabicyclo [4.2.0] oct-2-en-8-oxo-2-carboxylic acid obtained in Example 1 as such in the crystal form is added to the thus prepared dimethylformamide solution with ice cooling. The mixture is subjected to reaction at room temperature for 18 hours. The reaction mixture is concentrated and 100 ml of chloroform and 100 ml of water are added to the residue to make a solution. Then, the organic layer is separated therefrom and washed with water and then with an aqueous saturated sodium chloride solution. The thus obtained chloroform layer is dried and concentrated, and the residue is purified by column chromatography using 50 g of silica gel (eluting solvent: chloroform), whereby 0.89 g of white powder is obtained. The powder has the following physical properties and is identified to be the captioned compound (yield: 69%).

NMR (CDCl$_3$) δ (ppm): 7.8 (4H, m), 5.67 (1H, d), 4.10 (3H, s), 3.9 (1H, m), 2.9–1.8 (4H, m), 1.56 (9H, s).

EXAMPLE 3

Preparation of (±)-cis-7-amino-3-methanesulfonyloxy-1-azabicyclo [4.2.0] oct-2-en-8-oxo-2-carboxylic acid At first, 10 ml of methylene chloride and 10 ml of trifluoroacetic acid are added to 4.6 g of tertiary butyl ester of (±)-cis-7-phthalimido-3-methanesulfonyloxy-1-azabicyclo [4.2.0] oct-2-en-8-oxo-2-carboxylic acid, and the resultant solution is subjected to reaction at room temperature for one hour. The reaction mixture is concentrated to dryness, and 20 ml of chloroform is added to the thus obtained white solid, and the mixture is concentrated under reduced pressure. This cycle of operation is repeated twice, and the solid is completely dried under reduced pressure.

The solid is suspended in 220 ml of water, and the suspension is adjusted to pH 7 with an aqueous saturated sodium bicarbonate solution. Then, 0.83 ml of methylhydrazine is added thereto dropwise with ice cooling over 45 minutes, and the mixture is subjected to reaction at room temperature for 3 hours. The reaction mixture is adjusted to pH 1 with concentrated hydrochloric acid, and the deposited crystals are removed therefrom by filtration. The filtrate is adjusted to pH 3.5 with an aqueous saturated sodium bicarbonate solution, and concentrated to a liquid volume of 50 ml. Then, the solution is left standing in a refrigerator overnight, and the deposited crystals are removed therefrom by filtration, whereby 1.82 g of white columnar crystals are obtained. The crystals have the following physical properties and are identified to be the captioned compound (yield: 66.2%).

IR ν max (KBr) (cm$^{-1}$): 1800, 1650, 1620, 1560, 1545, 1535.

EXAMPLE 4

Preparation of (6R, 7S) 7-[(R)-phenylglycylamino]-3-methanesulfonyloxy-1-azabicyclo [4.2.0] oct-2-en-8-oxo-2-carboxylic acid At first, 460 mg of (±) cis-7-amino-3-methanesulfonyloxy-1-azabicyclo [4.2.0] oct-2-en-8-oxo-2-carboxylic acid synthesized according to the procedure of Example 3 is dissolved in 20 ml of 1/10M phosphate buffer (pH 7.0), and 1.5 g of phenylglycine methyl ester hydrochloride and 10 ml of immobilized enzyme having a penicillin acylase activity (whose preparatory method is disclosed in Japanese Published Unexamined Patent Application No. 138396/1980 and EP No. 0014476) are added thereto. The mixture is shaken at 30° C. for 1.5 hours while adjusting the mixture to pH 7.0 with 1N potassium hydroxide. The immobilized enzyme is removed therefrom by filtration, and the filtrate is adjusted to pH 3.0 with 1N hydrochloric acid, and concentrated to about 5 ml under reduced pressure. The precipitates are removed therefrom by filtration, and the filtrate is purified by column chromatography using 100 ml of Diaion HP-10 (eluting solvent: water:methanol=2:1), whereby 210 ml of white powder is obtained.

The powder has the following physical properties and is identified to be the captioned compound [yield: 62% (in the reaction, optical resolution of the skeleton is carried out at the same time, and the apparent yield is 31%, but since the raw material is a dl compound, and thus the reaction itself has a yield of 62%; in the following Examples, the yield based on such an operation is also described)].

IR ν max (KBr) (cm$^{-1}$): 1770, 1700, 1630, 1610, 1540.
NMR (D$_2$O) δ (ppm): 7.55 (5H, s), 5.41 (1H, d, J=5.2 Hz), 5.21 (1H, s), 3.9 (1H, m), 3.30 (3H, s), 2.7–2.3 (2H, m), 1.8–1.1 (2H, m).

EXAMPLE 5

Preparation of (±)-cis-7-amino-3-(1-methyl-1,2,3,4-tetrazol-5-yl-thio)-1-azabicyclo [4.2.0] -oct-2-en-8-oxo-2-carboxylic acid At first, 1.2 g of tertiary butyl ester of (±)-cis-7-phthalimido-3-(1-methyl-1,2,3,4-tetrazol-5-yl-thio)-1-azabicyclo [4.2.0]-oct-2-en-8-oxo-2-carboxylic acid synthesized according to Example 2 is dissolved in 12 ml of dimethylformamide, and 0.20 ml of methylhydrazine is added thereto with ice cooling. The mixture is subjected to reaction at room temperature for 2 hours, and the solvent is removed therefrom by distillation under reduced pressure. Then, 50 ml of water and 50 ml of ethyl acetate are added to the residue, and the aqueous layer is adjusted to pH 1.5 with 1N hydrochloric acid and separated therefrom. The aqueous layer is adjusted to pH 7.0 with an aqueous saturated sodium bicarbonate solution, and twice extracted with 50 ml of ethyl acetate. The extracts are joined together, and washed with water and an aqueous saturated sodium chloride solution, and then concentrated to dryness. The residue (about 1 g) is dissolved in 5 ml of methylene chloride and 5 ml of trifluoroacetic acid, and the solution is subjected to reaction for one hour with ice cooling. The reaction solution is concentrated to dryness under reduced pressure, and 10 ml of chloroform is added thereto. The mixture is again concentrated to dryness. The residue is dissolved in water, and the solution is adjusted to pH 3.5 with an aqueous saturated sodium bicarbonate solution and purified by column chromatography using 100 ml of Diaion HP-10 (eluting solvent: water:methanol=10:1), whereby 390 mg of white powder is obtained. The powder has the following physical properties and is identified to be the captioned compound (yield: 55%).

IR $\nu$ max (KBr)(cm$^{-1}$): 1800, 1680, 1630, 1550.

EXAMPLE 6

Preparation of (±)-cis-7-[2-(2-aminothiazol-4-yl) 2-syn-methoxyimino-acetamido]-3-methanesulfonyloxy-1-azabicyclo [4.2.0] oct-2-en-8-oxo-2-carboxylic acid At first, 663 mg of 2-tritylaminothiazol-4-yl-2-syn-methoxyiminoacetic acid is dissolved in 10 ml of tetrahydrofuran, and the solution is cooled to −20° C. Then, 0.21 ml of tritylamine and 312 mg of phosphorus pentachloride are added to the solution, and the mixture is subjected to reaction at the same temperature for one hour to make an acid chloride solution.

Separately, 390 mg of (±)-cis-7-amino-3-methanesulfonyloxy-1-azabicyclo [4.2.0] oct-2-en-8-oxo-2-carboxylic acid is dissolved in 10 ml of water and 5 ml of tetrahydrofuran, and the solution is adjusted to pH 6.5 with an aqueous saturated sodium bicarbonate solution. Then, said acid chloride solution is added dropwise thereto with ice cooling while keeping the solution at pH 6-7. After the end of dropwise addition, the mixture is subjected to reaction at room temperature for one hour, then adjusted to pH 2 with 1N hydrochloric acid and twice extracted with 20 ml of ethyl acetate. The extracts are joined together, washed with an aqueous saturated sodium chloride solution, and concentrated to dryness. The residue is dissolved in 20 ml of methanol, and the solution is adjusted to pH 1.2 with 1N hydrochloric acid and subjected to reaction at 40° C. for 1.5 hours. The reaction solution is concentrated and purified by column chromatography using 50 ml of Diaion HP-10, whereby 260 mg of light yellow powder is obtained. The powder has the following physical properties and is identified to be the captioned compound (yield: 56.6%).

IR $\nu$ max (KBr)(cm$^{-1}$): 1770, 1660, 1630, 1560, 1550, 1365, 1200.

NMR (DMSOd6-CD$_3$OD) $\delta$ (ppm): 6.78 (1H, s), 5.49 (1H, d), 3.90 (3H s), 3.8 (1H, m), 3.26 (3H, s), 2.9–2.5 (2H, m), 2.3–1.7 (2H, m)

EXAMPLE 7

Preparation of (±)-cis-7-amino-3-(4-pyridylthio)-1-azabicyclo [4.2.0] oct-2-en-8-oxo-2-carboxylic acid The same operations as in Example 2 are carried out except that 0.92 g of 4-mercaptopyridine is used in place of 1.2 g of 1-methyl-5-mercapto-1,2,3,4-tetrazole, and the thus obtained powder is treated in the same manner as in Example 5 (where the eluting solvent for the column chromatography of Diaion HP-10 is water), whereby 420 mg of light yellow crystals is obtained. The crystals have the following physical properties and are identified to be the captioned compound (yield: 41%).

NMR (D$_2$O) $\delta$ (ppm): 8.0 (2H, d), 7.28 (2H, d), 4.50 (1H, d, J =5.1), 3.8 (1H, m), 2.3–1.3 (4H, m).

EXAMPLE 8

Preparation of (±)-cis-7-[2-(2-aminothiazol-4-yl)2-syn-methoxyiminoacetamido]-3 (1-methyl-1,2,3,4-tetrazol--5-yl-thio)-1-azabicyclo[4.2.0] oct-2-en-8-oxo-2-carboxylic acid The same operations as in Example 8 are carried out except that 410 mg of (±)-cis-7-amino-3-(1-methyl-1,2,3,4-tetrazol-5-yl-thio)-1-azabicyclo [4.2.0] oct-2-en-8-oxo-2-carboxylic acid synthesized according to Example 5 is used in place of 390 mg of (±)-cis-7-amino-3-methanesulfonyloxy-1-azabicyclo [4.2.0] oct-2-en-8-oxo-2-carboxylic acid (where the eluting solvent for the column chromatography of Diaion HP-10 is water:methanol=5:1), whereby 210 mg of white powder is obtained. The powder has the following physical properties and is identified to be the captioned compound (yield: 32.4%).

NMR (D$_2$O) $\delta$ (ppm): 6.91 (1H, s), 5.47 (1H, d), 4.03 (3H, s), 3.93 (3H, s), 3.8 (1H, m), 2.6–1.4 (4H, m).

EXAMPLE 9

Preparation of (6R, 7S)-7-[(R)-phenylglycylamino]-3-(1,2,3-thiadiazol-5-yl-thio)-1-azabicyclo [4.2.0] oct-2-en-8-oxo-2-carboxylic acid At first, 480 mg of benzhydryl ester of (6R, 7S)-7-[2-(R)-t-butoxycarbonylamino-2-phenyl-acetamido]-3-methane-sulfonyloxy-1-azabicyclo [4.2.0] oct-2-en-8-oxo-2-carboxylic acid is dissolved in 5 ml of dimethylformamide, and 210 mg of 5-mercapto-1,2,3-thiadiazole sodium salt is added thereto. The mixture is subjected to reaction at 50° C. for 2 hours. The reaction solution concentrated, and 50 ml of ethyl acetate and 50 ml of water are added thereto. The organic layer is separated therefrom, washed twice with water, and dried over anhydrous sodium sulfate. The solvent is removed therefrom by distillation under reduced pressure, whereby 405 mg of yellow powder is obtained, the powder is dissolved in 5 ml of methylene chloride and 0.5 ml of anisole, and 5 ml of trifluoroacetic acid is added thereto with ice cooling. The mixture is subjected to reaction at the same temperature for one hour. The reaction solution is concentrated and then 20 ml of ether is added thereto to deposit solids. The solids are separated therefrom by filtration, and dissolved into 2 ml of water. The solution is purified by column chromatography using 100 ml of Diaion HP-10 (eluting solvent:

water:methanol=1:1), whereby 120 mg of white powder is obtained. The powder has the following physical properties and are identified to be the captioned compound (yield: 55.6%).

IR ν max (KBr)(cm$^{-1}$): 1770, 1695, 1575, 1510.

NMR (CD$_3$OD) δ (ppm): 8.53 (1H, s), 7.40 (5H, s), 5.38 (1H, d), 5.13 (1H, s), 3.8 (1H, m), 2.4–2.1 (2H, m), 1.2–1.8 (2H, m).

EXAMPLE 10

Preparation of (±)-cis-7-[2-(2-aminothiazol-4-yl)-2-syn-methoxyimino-acetamido]-3-(1-methyl-pyridinium-4-yl-thio)-1-azabicyclo [4.2.0]oct-2-en-8-oxo-2-carboxylate (10-1) Preparation of benzhydryl ester of (±)-cis-7-[2-(2-tritylaminothiazol-4-yl)-2-syn-methoxyiminoacetamido]-3-methanosulfonyloxy-1-azabicyclo [4.2.0] oct-2-en-8-oxo-2- carboxylic acid At first, 1.32 g of 2-tritylamino-thiazol-4-yl-2-syn-methoxyiminoacetic acid is dissolved in 20 ml of tetrahydrofuran, and the solution is cooled to −20° C. Then, 0.64 g of phosphorus pentachloride and 0.44 ml of triethylamine are added thereto, and the mixture is stirred at the same temperature for one hour to make an acid chloride solution.

Separately, 1.2 g of (±)-cis-7-amino-3-methanesulfonyloxy-1-azabicyclo [4.2.0] oct-2-en-8-oxo-2carboxylic acid is added to 30 ml of water and 15 ml of tetrahydrofuran, and the mixture is adjusted to pH 7.0 to make a solution. Then, said acid chloride solution is added dropwise to the solution with ice cooling and stirring, while keeping the solution at pH 7. After the end of dropwise addition, the mixture is subjected to reaction with ice cooling for one hour, and the reaction solution is adjusted to pH 2.5. Then, 50 ml of ethyl acetate is added thereto, and the organic layer is separated therefrom, and concentrated under reduced pressure. The residue is dissolved in 20 ml of chloroform, and 2.3 g of diphenyldiazomethane is added thereto with stirring. The mixture is subjected to reaction for 30 minutes, concentrated and purified by column chromatogrpaphy using 200 ml of silica gel (eluting solvent: hexane:ethyl acetate=1:1), whereby 1.8 g of white powder is obtained. The powder has the following physical properties and is identified to be the captioned compound (yield: 67.4%).

NMR (CDCl$_3$-CD$_3$OD) δ (ppm): 7.5–7.2 (25H, m), 6.93 (1H, s), 6.65 (1H, s), 5.50 (1H, d), 3.99 (3H, s), 4 (1H, m), 2.90 (3H, s), 2.9–2.4 (2H, m), 2.3–1.5 (2H, m).

(10-2) Preparation of (±)-cis-7-[2-(2-aminothiazol-4-yl)-2-syn-methoxyimino-acetamido]-3-(1-methylpyridinium-4-yl-thio)-1-azabicyclo [4.2.0] oct-2-en-8-oxo-2-carboxylate At first, 600 mg of the compound synthesized in (10-1) is dissolved in 5 ml of dimethylformamide, and 4-mercaptopyridine sodium salt prepared from 135 mg of 4-mercaptopyridine and 48 mg of sodium hydride (50%) is added to the solution. The mixture is subjected to reaction at room temperature for 3 hours. The reaction mixture is concentrated under reduced pressure, and 50 ml of ethyl acetate and 50 ml of water are added to the residue. The organic layer is separated therefrom, and washed with water, and the solvent is removed therefrom by distillation, whereby light yellow powder is obtained. The powder is dissolved in chloroform, and the solution is purified by column chromatography using 50 ml of silica gel (eluting solvent: hexane:ethyl acetate=1:2), whereby 330 mg of white powder is obtained. Then, 230 mg of the powder is dissolved in 10 ml of methylene chloride, and 0.1 ml of methyl iodide is added thereto. The mixture is subjected to reaction at room temperature overnight in a tightly shut state. The reaction solution is concentrated to dryness, and 255 mg of the resulting solid is dissolved in 4 ml of methylene chloride and 1 ml of anisole. Then, 4 ml of trifluoroacetic acid is added thereto with cooling, and the mixture is subjected to reaction for one hour. The reaction solution is concentrated under reduced pressure, and 2 ml of water is added to the residue. The mixture is purified by column chromatography using 30 ml of Diaion HP-10 (eluting solvent: water:methanol=5:1), whereby 84 mg of white powder is obtained. The powder has the following physical properties and is identified to be the captioned compound (yield: 39.4%).

NMR (DMSOd6-D$_2$O) δ (ppm): 8.40 (2H, d), 7.66 (2H, d), 6.74 (1H, s), 5.37 (1H, d, J=5.6 Hz), 4.09 (3H, s), 3.95 (3H, s), 3.8 (1H, m), 2.5–1.2 (4H, m).

EXAMPLE 11

Preparation of (6R, 7S)-7-[(R)-phenylglycylamino]-3-(1-methylpyridinium-4-yl-thio)-1-azabicyclo [4.2.0] oct-2-en-8-oxo-2-carboxylate (11-1) Preparation of benzhydryl ester of (6R, 7S)-7-[2-(R)-t-butoxycarbonylamino-2-phenylacetamido]-3-methanesulfonyloxy-1-azabicyclo [4.2.0] -oct-2-en-8-oxo-2-carboxylic acid At first, 1.36 g of (6R, 7S)-7-[2-(R)-phenylglycylamino]-3-methanesulfonyloxy-1-azabicyclo [4.2.0] oct-2-en-8-oxo-2-carboxylic acid synthesized according to Example 4 is dissolved in 20 ml of water and 20 ml of tetrahydrofuran, and the solution is adjusted to pH 7.0 with an aqueous saturated sodium bicarbonate solution. Then, 4 ml of a tetrahydrofuran solution containing 1.5 g of di-t-butyl dicarbonate is added dropwise to the solution at room temperature with stirring, while keeping the solution at pH 7. After the end of dropwise addition, the mixture is subjected to reaction at room temperature for two hours, and then 20 ml of ethyl acetate is added thereto. Then, the aqueous layer is separated therefrom, adjusted to pH 1.9 with 1N hydrochloric acid, and extracted twice with 50 ml of ethyl acetate. The extracted organic layers are joined together, washed with water and an aqueous saturated sodium chloride solution, dried over anhydrous sodium sulfate and concentrated to dryness. The residue is dissolved in 20 ml of chloroform, and 1.5 g of diphenyldiazomethane is added thereto. The mixture is subjected to reaction at room temperature for 30 minutes. The reaction solution is concentrated and then purified by column chromatography using 200 ml of silica gel, whereby 1.42 g of white powder is obtained. The powder has the following physical properties is identified to be the captioned compound (yield: 63.3%).

NMR (CDCl$_3$) δ (ppm): 7.5–7.2 (15H, m), 6.90 (1H, s), 6.8 (1H, d), 5.65 (1H, d), 5.37 (1H, dd), 5.16 (1H, d), 3.8 (1H, m), 2.83 (3H, s), 2.7–2.4 (2H, m), 1.38 (9H s), 1.9–1.3 (2H, m).

(11-2) Preparation of (6R, 7S)-7-[(R)-phenylglycylamino]-3-(1-methylpyridinium-4-yl-thio)-1-azabicyclo [4.2.0] oct-2-en-8-oxo-2-carboxylate At first, 570 mg of the compound obtained in (11-1) is dissolved in 10 ml of dimethylformamide, and 220 mg of 4-mercaptopyridine and 0.2 ml of triethylamine are added thereto. The mixture is subjected to reaction at 50° C. for 4 hours. The reaction solution is concentrated to dryness under reduced pressure, and 60 ml of ethyl acetate and 60 ml of water are added to the residue. The organic layer is separated, and washed with water and an aqueous saturated sodium chloride solution, and then the solvent is removed therefrom by distillation under reduced pressure. The thus obtained yellow powder is dissolved in 5 ml of methylene chloride, and 0.2 ml of methyl iodide is added thereto. The mixture is subjected to reaction at room temperature overnight. The reaction solution is again concentrated, and the residue. is dissolved again in 5 ml of methylene chloride and 0.5 ml of anisole, and 5 ml of trifluoroacetic acid is added thereto with cooling. The mixture is stirred for one hour. The reaction solution is concentrated, and the residue is dissolved in water, and the solution is purified by column chromatography using 50 ml of Diaion HP-10, whereby 140 mg of white powder is obtained. The powder has the following physical properties and is identified to be the captioned compound (yield: 31.6%).

NMR (D$_2$O) δ (ppm): 8.40 (2H, d), 7.66 (2H, d), 7.51 (5H, s), 5.49 (1H, d), 5.28 (1H, s), 4.12 (3H, s), 3.9 (1H, m), 2.5–1.4 (4H, m).

EXAMPLE 12

Preparation of (±)-cis-7-[2-(2-aminothiazol-4-yl)-2-syn-methoxyiminoacetamido]-3-(2-methyl-1,3,4-thiadiazolyl-5-thio)-1-azabicyclo [4.2.0] oct-2-en-8-oxo-2-carboxylic acid At first, 380 mg of benzhydryl ester of (±)-cis-7-[2-(2-tritylaminothiazol-4-yl)-2-syn-methoxyiminoacetamido]-3-methanesulfonyloxy-1-azabicyclo [4.2.0]oct-2-en-8-oxo-2-carboxylic acid obtained in Example (10-1) is dissolved in 5 ml of dimethylformamide, and a sodium salt prepared from 36 mg of sodium hydride (50%) and 130 mg of 2-methyl-5-mercapto-1,3,4-thiadiazole is added thereto. The mixture is subjected to reaction at 60° C. for 3 hours. The reaction solution is concentrated under reduced pressure, and the residue is dissolved in 50 ml of ethyl acetate and 50 ml of water. The organic layer is separated therefrom, washed with water, and dried over anhydrous sodium sulfate, and the solvent is removed therefrom by distillation under reduced pressure. Then, 2 ml of methylene chloride and 0.2 ml of anisole are added to the thus obtained light brown powder, and 2 ml of trifluoroacetic acid is added thereto with ice cooling. The mixture is subjected to reaction for one hour. The reaction solution is concentrated, and the residue is purified by column chromatography using 50 ml of Diaion HP-10 (eluting solvent: water:methanol=2:1), whereby 96 mg of white powder is obtained. The powder has the following physical properties and is identified to be the captioned compound (yield: 37.9%).

NMR (DMSOd6-CD$_3$OD) δ (ppm): 6.65 (1H, s), 5.45 (2H, d), 3.93 (3H, s), 3.8 (1H, m), 2.71 (3H, s), 1.2–2.6 (4H, m)

EXAMPLE 13

Preparation of (6R, 7S)-7-[(R)-phenylglycinamido]-3-(1-methyl-1,2,3,4-tetrazol-5-yl)-thio-1-azabicyclo [4.2.0] oct-2-en-8-oxo-2-carboxylic acid The same operations as in Example 4 are carried out except that 510 mg of (±)-cis-7-amino-3-(1-methyl-1,2,3,4-tetrazol-5-yl)-thio-1-azabicyclo [4.2.0] oct-2-en-8-oxo-2-carboxylic acid synthesized according to Example 5 is used in place of 460 mg of (±)-cis-7-amino-3-methanesulfonyloxy-1-azabicyclo [4.2.0] oct-2-en-8-oxo-2-carboxylic acid, whereby 160 mg of the captioned compound is obtained (yield: 47%).

NMR (D$_2$O) δ (ppm): 7.40 (5H, s), 5.33 (1H, d), 5.08 (1H, s), 3.98 (3H, s), 3.8 (1H, m), 2.2–1.4 (4H, m).

EXAMPLE 14

Preparation of (6R, 7S)-7-[(R)-phenylglycinamido]-3-(4-pyridylthio)-1-azabicyclo [4.2.0]oct-2-en-8-oxo-2-carboxylic acid The same operations as in Example 4 are carried out except that (±)-cis-7-amino-3-(4-pyridyl-thio)-1-azabicyclo [4.2.0] oct-2-en-8-oxo-2-carboxylic acid synthesized according to Example 7 is used in place of (±)-cis-7-amino-3-methanesulfonyloxy-1-azabicyclo [4.2.0]oct-2-en-8-oxo-2-carboxylic acid, whereby 110 mg of the captioned compound is obtained (yield: 52%).

IR ν max (KBr)(cm$^{-1}$): 1790, 1710, 1700, 1630, 1560.

NMR (D$_2$O+DCl) δ (ppm): 8.33 (2H, d), 7.92 (2H, d), 7.40 (5H, s), 5.32 (1H, d), 5.10 (1H, s), 3.8 (1H, m), 2.4–1.4 (4H, m).

EXAMPLE 15

Preparation of (±)-cis-7-[2-(2-aminothiazol-4-yl)-2-syn-methoxyiminoacetamido]-3-azido-1-azabicyclo [4.2.0]oct-2-en-8-oxo-2-carboxylic acid The same operations as in Example 12 are carried out except that 65 mg of sodium azide is used in place of 2-methyl-5-mercapto-1,3,4-thiadiazole sodium salt (where the eluting solvent for the column chromatography is water:methanol=1:2), whereby 82 mg of the captioned compound is obtained (yield: 40.4%).

IR 84 max (KBr)(cm$^{-1}$):2120, 1775, 1770, 1755, 1685, 1670, 1545.

EXAMPLE 16

Preparation of (6R, 7S)-7-[(R)-phenylglycinamido]-3-(2-pyridyl)-thio-1-azabicyclo [4.2.0]oct-2-en-8-oxo-2-carboxylic acid The same operations as in Example 9 are carried out except that 2-mercaptopyridine sodium salt is used in place of 5-mercapto-1,2,3-thiadiazole sodium salt, whereby 112 mg of the captioned compound is obtained (yield: 71%).

IR ν max (KBr)(cm$^{-1}$): 1775, 1695, 1580. NMR (D$_2$O-DCl) δ (ppm): 8.2–8.7 (2H, m), 7.7–8.0 (2H, m), 7.50 (5H, s), 5.33 (1H, d, J=5.4 Hz), 5.20 (1H, s), 3.9 (1H, m), 2.5–2.2 (2H, m), 1.8–1.0 (2H, m).

EXAMPLE 17

Preparation of (6R, 7S)-7-[(R)-phenylglycinamido]-3-(2-methyl-1,3,4-thiadiazol-5-yl) thio-1-azabicyclo [4.2.0]oct-2-en-8-oxo-2-carboxylic acid The same operations as in Example 9 are carried out except that 2-mercapto-5-methyl-1,3,4-thiadiazole sodium salt is used in place of 5-mercapto-1,2,3-thiadiazole sodium salt, whereby 62 mg of the captioned compound is obtained (yield: 30%).

IR $\nu$ max (KBr)(cm$^{-1}$): 1780, 1695, 1605. NMR (D$_2$O-DCl) $\delta$ (ppm): 7.40 (5H, s), 5.38 (1H, d, J=5.0 Hz), 5.13 (1H, s), 3.9 (1H, m), 2.69 (3H, s), 2.4–1.0 (4H, m).

EXAMPLE 18

Another route for the preparation of (6R, 7S)-7-[(R)-phenylglycinamido]-3-(4-pyridylthio)-1-azabicyclo [4.2.0]oct-2-en-8-oxo-2-carboxylic acid (18-1) Preparation of benzhydryl ester of (6R, 7S)-7-[2-(R)-t-butoxycarbonylamino-2-phenylacetamido]-3-chloro-1-azabicyclo [4.2.0]oct-2-en-8-oxo-2-carboxylic acid At first, 940 mg of (6R, 7S)-7-[(R)-phenylglycinamido]-3-chloro-1-azabicyclo [4.2.0]oct-2-en-8-oxo-2-carboxylic acid (the compound is disclosed in Japanese Published Unexamined Patent Application No. 16491/1981 (equate EP No. 14476) and EP No. 0014476A1) is added to 15 ml of water and 15 ml of tetrahydrofuran, and the mixture is adjusted to pH 7.0 with an aqueous saturated sodium bicarbonate solution. Then, 1.1 g of di-t-butyl dicarbonate is added thereto by portions over 30 minutes, and the mixture is subjected to reaction for 3 hours, whereby a homogeneous solution is obtained. Then, 20 ml of water and 20 ml of ethyl acetate are added to the reaction solution, and the aqueous layer is separated therefrom, adjusted to pH 2 with an aqueous 10% citric acid solution, and extracted twice with 50 ml of ethyl acetate. The extract is washed with an aqueous saturated sodium chloride, and concentrated to dryness, and the thus obtained powder is dissolved in 50 ml of chloroform. Then, 1.1 g of diphenyldiazomethane is added thereto with stirring, and the mixture is subjected to reaction for 30 minutes. The reaction solution is concentrated to about 10 ml, and the concentrate is added to 100 ml of hexane dropwise. The precipitated white powder is recovered therefrom by filtration, whereby 1.25 g of the captioned compound is obtained (yield: 75.5%).

NMR (CDCl$_3$-CD$_3$OD) $\delta$ (ppm): 7.5–7.1 (15H, m), 6.91 (1H, s), 5.38 (1H, d), 5.18 (1H, s), 3.8 (1H, m), 2.6–2.3 (2H, m), 1.8–1.2 (2H, m), 1.40 (9H, s).

(18-2) Preparation of (6R, 7S)-7-[(R)-phenylglycinamido]-3-(4-pyridylthio)-1-azabicyclo [4.2.0] oct-2-en-8-oxo-2-carboxylic acid The same operations as in Example 9 are carried out except that benzhydryl ester of (6R, 7S)-7-[2-(R)-t-butoxycarbonylamino-2-phenylacetamido]-3-chloro-1-azabicyclo [4.2.0]oct-2-en-8-oxo-2-carboxylic acid is used in place of benzhydryl ester of (6R, 7S)-7-[2-(R)-t-butoxycarbonylamino-2-phenylacetamido]-3-methanesulfonyloxy 4-mercaptopyridine sodium salt is used in place of 5-mercapto-1,2,3-thiadiazole sodium salt, whereby 118 mg of white powder is obtained.

The powder is completely identical with the powder obtained in Example 14 in IR and NMR and is identified to be the captioned compound (yield: 54.2%).

REFERENCE EXAMPLE 1

Preparation of tertiary butyl ester of (±)-cis-7-phthalimido-1-azabicyclo [4.2.0] oct-2,3-epoxy-8-oxo-2-carboxylic acid At first, 18.4 g of tertiary buthyl ester of (±)-cis-7-phthalimido-1-azabicyclo [4.2.0] oct-2-en-8-oxo-2-carboxylic acid is suspended in 400 ml of tetrahydrofuran and 100 ml of water, and 8.3 g of N-bromosuccinimide is added thereto by portions with adequate stirring over one hour. After the end of addition, the mixture is subjected to reaction at room temperature for 2 hours, and 400 ml of ethyl acetate is added to the reaction solution. The organic layer is separated therefrom, washed twice with 500 ml of water, washed with an aqueous saturated sodium chloride solution and dried over anhydrous sodium sulfate, and the solvent is removed therefrom by distillation under reduced pressure, whereby light yellow solid is obtained. The solid is dissolved in 300 ml of chloroform, and 7.0 ml of 1,8-diazabicyclo [5.4.0] undecene is added thereto with ice cooling. The mixture is subjected to reaction for 2 hours. Then, 200 ml of chloroform and 400 ml of water are added to the reaction solution, and the organic layer is separated therefrom, washed with 400 ml of an aqueous 10% citric acid solution and an aqueous saturated sodium chloride solution, and the chloroform layer is dried over anhydrous sodium sulfate and then concentrated under reduced pressure, whereby light yellow oily substance is obtained. The oily substance is crystallized from 100 ml of solvent mixture of hexane:ethyl acetate=1:1, and the deposited crystals are recovered therefrom by filtration, whereby 12.2 g of white, needle-like crystals is obtained. The crystals have the following physical properties and are identified to be the captioned compound (yield: 63.5%).

NMR (CDCl$_3$) $\delta$ (ppm): 7.8 (4H, m), 5.55 (1H, d, J=5.2 Hz), 3.7 (1H, m), 3.65 (1H, m), 2.5–1.6 (4H, m), 1.52 (9H, s).

IR $\nu$ max (KBr)(cm$^{-1}$): 1795, 1790, 1775, 1735, 1720, 1395.

REFERENCE EXAMPLE 2

The antibacterial effects of the present compounds by dilution method on Mueller-Hinton agar (pH 7.2) are shown in Table 1 (MIC $\mu$g/ml). Compound Number designates Example Number where the process for preparing the compound in question is described.

TABLE 1

| Compound No. (Ex. No.) | Bacteria used for test | | | |
|---|---|---|---|---|
| | Staphylococcus aureus 209P | Staphylococcus epidermidis F-1 | Escherichia coli NIHJ JC-2 | Klebsiella pneumoniae KY8045 |
| 4 | 0.39 | 0.78 | 1.56 | 0.78 |
| 6 | 12.5 | 12.5 | 0.39 | 0.39 |
| 8 | 0.39 | 3.13 | 0.1 | 0.05 |
| 9 | 0.1 | 0.39 | 0.39 | 0.1 |
| 10 | 0.78 | 0.78 | 0.01 | 0.01 |
| 11 | 0.05 | 0.39 | 1.56 | 0.78 |
| 12 | 0.78 | 3.13 | 0.1 | 0.05 |
| 13 | 0.2 | 0.78 | 1.56 | 0.78 |
| 14 | 0.1 | 0.39 | 0.39 | 0.1 |
| 17 | 0.1 | 0.39 | 0.78 | 0.39 |

What is claimed is:

1. A carbacephem compound represented by the formula:

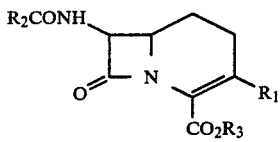

wherein:
R$_1$ is unsubstituted or substituted heterocyclicthio group, wherein the heterocyclic group is apyridyl, tetrazolyl, thiazolyl, thiadiazolyl, oxazolyl, triazolyl, pyrimidyl, imdazolyl or triazinyl group, and the substituent on these heterocycles is an alkyl group having 1 to 6 carbon atoms, hydroxyl, amino, nitro or —(CH$_2$)$_n$ Y group, wherein Y is a hydroxyl, carboxyl or sulfo group, and n is an integer of 1 to 4;
R$_2$ is a group represented by the formula:

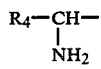

wherein R$_4$ is a phenyl group optionally substituted with an alkyl group having 1 to 6 carbon atoms, hydroxyl, amino, nitro or carboxyl group, or 2-aminothaizolyl group, or a group represented by the formula:

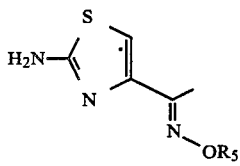

wherein R$_5$ is an alkyl group having 1 to 7 carbon atoms optionally substituted with a hydroxyl, carboxyl or sulfo group;
R$_3$ is hydrogen, an alkali metal, an alkaline earth metal, an ammonium group of a basic amino acid, a group represented by the formula:

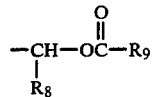

where R$_8$ is hydrogen or an alkyl group having 1 to 6 carbon atoms, and R$_9$ is an alkyl group having 1 to 6 carbon atoms or phenyl group, or a group represented by the formula:

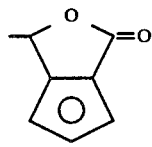

2. A carbacephem compound represented by the formula:

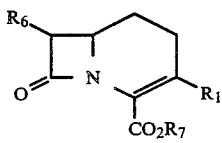

wherein:
R$_1$ is an unsubstituted or substituted heterocyclicthio group, wherein the heterocyclic group is a pyridyl, tetrazolyl, thaizolyl, thiadiazolyl, oxazolyl, triazolyl, pyrimidyl, imidazolyl or triazinyl group, and the substituent on these heterocycles is an alkyl group having 1 to 6 carbon atoms, hydroxyl, amino, nitro or —(CH$_2$)$_n$ Y group, where Y is a hydroxyl, carboxyl or sulfo group, and n is an integer of 1 to 4;
R$_6$ is a phthalimido, azido or amino group; and
R$_7$ is hydrogen; a benzyl group optionally substituted with an alkyl group having 1 to 6 carbon atoms, hydroxy, amino, nitro or carboxyl group; a benzhydryl or alkyl group having 1 to 8 carbon atoms.

3. An antibacterial composition comprising, as an active ingredient, an effective amount of a compound of claim 1 in association with a pharmaceutical carrier or diluent.

* * * * *

UNITED STATES PATENT AND TRADEMARK OFFICE
CERTIFICATE OF CORRECTION

PATENT NO. : 4,640,919
DATED : February 3, 1987
INVENTOR(S) : KENICHI MOCHIDA, ET AL.

It is certified that error appears in the above-identified patent and that said Letters Patent is hereby corrected as shown below:

Title Page, at [54], "CARBACEPEM" should read --CARBACEPHEM--.

Column 1, line 1, "CARBACEPEM" should read --CARBACEPHEM--.

Column 5, line 59, "3-hydroxycarbacemphem" should read --3-hydroxycarbacephem--.

Column 15, line 31, "NMR(D$_2$/O" should read --NMR(D$_2$O)--.

Column 16, line 51, "IR 84" should read --IR υ--.

Column 17, line 66, after "methanesulfonyloxy" insert -- -1-azabicyclo [4.2.0] oct-2-en-8-oxo-2-carboxylic acid and--.

Column 19, line 13, "apyridyl," should read --a pyridyl,--.

line 31, "aminothaizolyl" should read --aminothiazolyl--.

Column 20, line 7, "where" should read --wherein--.

line 36, "where" should read --wherein--.

UNITED STATES PATENT AND TRADEMARK OFFICE
CERTIFICATE OF CORRECTION

PATENT NO. : 4,640,919

DATED : February 3, 1987

INVENTOR(S) : KENICHI MOCHIDA, ET AL.

It is certified that error appears in the above-identified patent and that said Letters Patent is hereby corrected as shown below:

Column 20, line 42, "hydroxy," should read --hydroxyl,--.

Signed and Sealed this

Twenty-first Day of April, 1987

Attest:

DONALD J. QUIGG

Attesting Officer     Commissioner of Patents and Trademarks